United States Patent
Sato et al.

(10) Patent No.: US 10,755,451 B2
(45) Date of Patent: Aug. 25, 2020

(54) IMAGE PROCESSING APPARATUS, IMAGE PROCESSING METHOD, COMPUTER-READABLE STORAGE MEDIUM, AND SYSTEM USING OPTICAL COHERENCE TOMOGRAPHY

(71) Applicant: CANON KABUSHIKI KAISHA, Tokyo (JP)

(72) Inventors: Makoto Sato, Tokyo (JP); Yoshihiko Iwase, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 124 days.

(21) Appl. No.: 16/007,267

(22) Filed: Jun. 13, 2018

(65) Prior Publication Data
US 2018/0365868 A1 Dec. 20, 2018

(30) Foreign Application Priority Data
Jun. 14, 2017 (JP) ................................ 2017-116757

(51) Int. Cl.
G06K 9/00 (2006.01)
G06T 11/00 (2006.01)
(Continued)

(52) U.S. Cl.
CPC .......... *G06T 11/005* (2013.01); *A61B 3/0025* (2013.01); *A61B 3/102* (2013.01);
(Continued)

(58) Field of Classification Search
CPC .. A61N 5/7203; A61N 5/0066; A61N 3/0025; A61N 3/102; A61N 6/032;
(Continued)

(56) References Cited

U.S. PATENT DOCUMENTS 9,170,087 B2 * 10/2015 Makihira ................ A61B 3/102
9,542,733 B2 * 1/2017 Nakamura .............. G06T 5/007
(Continued)

FOREIGN PATENT DOCUMENTS

JP H08-322838 A 12/1996
JP 2013000261 * 1/2013 ............... A61B 6/02
(Continued)

OTHER PUBLICATIONS

Michael et al, ("Optical Coherence tomography tor Ophthalmic Imaging", IEEE, 1995, pp. 67-76) (Year: 1995).*
(Continued)

*Primary Examiner* — Amara Abdi
(74) *Attorney, Agent, or Firm* — Venable LLP

(57) ABSTRACT

Provided is an image processing apparatus including: a data acquiring unit configured to acquire a plurality of pieces of tomographic data, which are obtained by performing optical coherence tomographic imaging of an object to be inspected through use of measuring light a plurality of times; a noise acquiring unit configured to acquire a noise characteristic of the tomographic data; a coefficient determining unit configured to determine a weighting coefficient corresponding to each pixel position in a tomographic image generated from the tomographic data based on the plurality of pieces of tomographic data and the noise characteristic; a changing unit configured to change a value of the tomographic data based on the weighting coefficient; and an image generating unit configured to generate the tomographic image based on the tomographic data that has the value changed.

17 Claims, 11 Drawing Sheets

(51) Int. Cl.
*A61B 3/10* (2006.01)
*A61B 3/00* (2006.01)
*A61B 5/00* (2006.01)
*G01B 9/02* (2006.01)
*A61B 6/03* (2006.01)
*G01N 23/046* (2018.01)
*G06T 5/00* (2006.01)

(52) U.S. Cl.
CPC .......... *A61B 5/0066* (2013.01); *A61B 5/7203* (2013.01); *A61B 6/032* (2013.01); *G01B 9/02091* (2013.01); *G01N 23/046* (2013.01); *G06T 5/002* (2013.01); *G06T 11/008* (2013.01); *G06T 2207/10101* (2013.01)

(58) Field of Classification Search
CPC .................. G06T 11/005; G06T 11/008; G06T 2207/10101; G06T 5/002; G01B 9/02091; G01N 23/046
See application file for complete search history.

(56) References Cited

U.S. PATENT DOCUMENTS

| | | | |
|---|---|---|---|
| 10,126,112 | B2 | 11/2018 | Sumiya et al. |
| 2011/0051088 | A1* | 3/2011 | Shimizu ................. A61B 3/102 |
| | | | 351/206 |
| 2012/0194661 | A1* | 8/2012 | Lee ........................... A61B 1/04 |
| | | | 348/68 |
| 2012/0274783 | A1 | 11/2012 | Ko et al. |
| 2016/0097632 | A1* | 4/2016 | Sumiya ............... G01B 9/02059 |
| | | | 356/479 |
| 2016/0253789 | A1* | 9/2016 | Chen ...................... H04N 5/145 |
| | | | 348/241 |

FOREIGN PATENT DOCUMENTS

| | | |
|---|---|---|
| JP | 2014-512245 A | 5/2014 |
| JP | 6046250 B2 | 12/2016 |
| WO | 2010/009447 A2 | 1/2010 |
| WO | 2012/149420 A1 | 11/2012 |

OTHER PUBLICATIONS

Aaron C. Chan, et al., "Maximum a posteriori estimator for high-contrast image composition of optical coherence tomography," Optics Letters, vol. 41, No. 2, Jan. 15, 2016, pp. 321-324.

Extended European Search Report dated Nov. 19, 2018, issued in European Application No. 18177278.1.

Aaron C. Chan, et al., "Noise-bias and polarization-artifact corrected optical coherence tomography by maximum a-posteriori intensity estimation," Biomedical Optics Express, vol. 8, No. 4, Apr. 2017, pp. 2069-2087.

* cited by examiner

IMAGE PROCESSING APPARATUS, IMAGE PROCESSING METHOD, COMPUTER-READABLE STORAGE MEDIUM, AND SYSTEM USING OPTICAL COHERENCE TOMOGRAPHY

BACKGROUND

Field

This disclosure relates to an image processing apparatus, an image processing method, and a computer-readable storage medium.

Description of the Related Art

In recent years, in the field of diagnostic imaging, imaging apparatus (OCT apparatus) using optical coherence tomography (OCT), which allows tomographic sections of a fundus and an anterior ocular segment to be observed and measured non-invasively, have become widespread. The OCT apparatus are widely used for various purposes from a research to a clinical purpose particularly in the field of ophthalmologic diagnosis.

A tomographic image of an eye to be inspected acquired by the OCT includes random noise ascribable to a detection system of the imaging apparatus and speckle noise ascribable to an object. Hitherto, as a method of reducing those kinds of noise, there has been widely used a method of acquiring a plurality of tomographic images at the same spot and averaging those tomographic images, to thereby suppress noise included in a single tomographic image to generate a finer tomographic image.

When an image of the fundus is acquired by the OCT, an image acquiring range of the OCT normally ranges from a vitreous body to a sclera in the depth direction (depth direction of the eye). With an improvement in performance of the OCT achieved in recent years, it is now possible to observe not only the structure of a retina but also the structure of the vitreous body. It is known that a change in structure of the vitreous body with aging causes a macular hole or other such dysfunction in the retina, and there has been a demand to observe the states of the retina and the vitreous body in detail.

In the related art for mainly observing the structure of a retinal layer, the contrast of a tomographic image has been adjusted so that it is easy to mainly observe the retinal layer. However, a signal intensity of a signal obtained from a vitreous body in the tomographic image acquired by the OCT is extremely much smaller than a signal intensity of a signal obtained from the retina. Therefore, when the contrast of the retinal layer is optimized, the contrast of the vitreous body is greatly reduced, or a pixel value is mapped to zero or a maximum value in the tomographic image, resulting in no visualization of the vitreous body. This cannot be solved even by the above-mentioned averaging processing.

Hitherto, histogram equalization has been known as a method of improving the contrast of an image as a whole. However, in histogram equalization processing, random noise components included in a tomographic image obtained by the OCT are also simultaneously emphasized to produce an image having high graininess, and hence the histogram equalization processing is not suitable for the observation of a minute structure of a vitreous body.

Therefore, according to Japanese Patent No. 6046250, there is proposed a method of optimizing the contrast of each region by dividing the region of a fundus into the region of a retinal layer and the region of a vitreous body based on the layer structure of the fundus and setting a display condition for each region. However, the above-mentioned method presupposes that region division is performed accurately, and in some cases, cannot be appropriately applied to a diseased eye that exhibits a large change in form of the layer structure and is thus difficult to be subjected to the accurate region division.

Meanwhile, according to Chan AC, Kurokawa K, Makita S, Miura M, Yasuno Y, "Maximum a posteriori estimator for high-contrast image composition of optical coherence tomography", Opt Lett., 2016; 41(2):321., doi:10.1364/OL.41.000321., there is proposed a method of performing a maximum a posteriori probability estimation (MAP estimation) on a signal intensity of the OCT based on a plurality of pieces of measurement data. In the proposed method, it is possible to increase a difference between the noise components overestimated in the related-art averaging processing and a signal obtained from the object to expand a dynamic range, and to easily separate the signal obtained from the object including the vitreous body from the noise components. However, there is still a difference in signal level between the retinal layer and the vitreous body, and hence when the contrast of any one of the retinal layer and the vitreous body is optimized, the contrast of the other one cannot be obtained. In addition, processing for the MAP estimation is generally numerical calculation using, for example, a gradient method, and may therefore be difficult to be used in a clinical site in which workflow is important due to a long calculation time period.

SUMMARY

Therefore, this disclosure provides an image processing apparatus, an image processing method, and a computer-readable storage medium, each of which is capable of simultaneously improving the contrasts of respective structures having a large difference in signal intensity in an OCT image of an object.

According to one embodiment of this disclosure, there is provided an image processing apparatus including: a data acquiring unit configured to acquire a plurality of pieces of tomographic data, which are obtained by performing optical coherence tomographic imaging of an object to be inspected through use of measuring light a plurality of times; a noise acquiring unit configured to acquire a noise characteristic of the tomographic data; a coefficient determining unit configured to determine a weighting coefficient corresponding to each pixel position in a tomographic image generated from the tomographic data based on the plurality of pieces of tomographic data and the noise characteristic; a changing unit configured to change a value of the tomographic data based on the weighting coefficient; and an image generating unit configured to generate the tomographic image based on the tomographic data that has the value changed.

According to another embodiment of this disclosure, there is provided an image processing method including: acquiring a plurality of pieces of tomographic data, which are obtained by performing optical coherence tomographic imaging of an object to be inspected through use of measuring light a plurality of times; acquiring a noise characteristic of the of tomographic data; determining a weighting coefficient corresponding to each pixel position in a tomographic image generated from the tomographic data based on the plurality of pieces of tomographic data and the noise characteristic; changing a value of the tomographic data based on the weighting coefficient; and generating the tomographic image based on the tomographic data that has the value changed.

Further features of the present invention will become apparent from the following description of exemplary embodiments with reference to the attached drawings.

DESCRIPTION OF THE EMBODIMENTS

Figure 1:
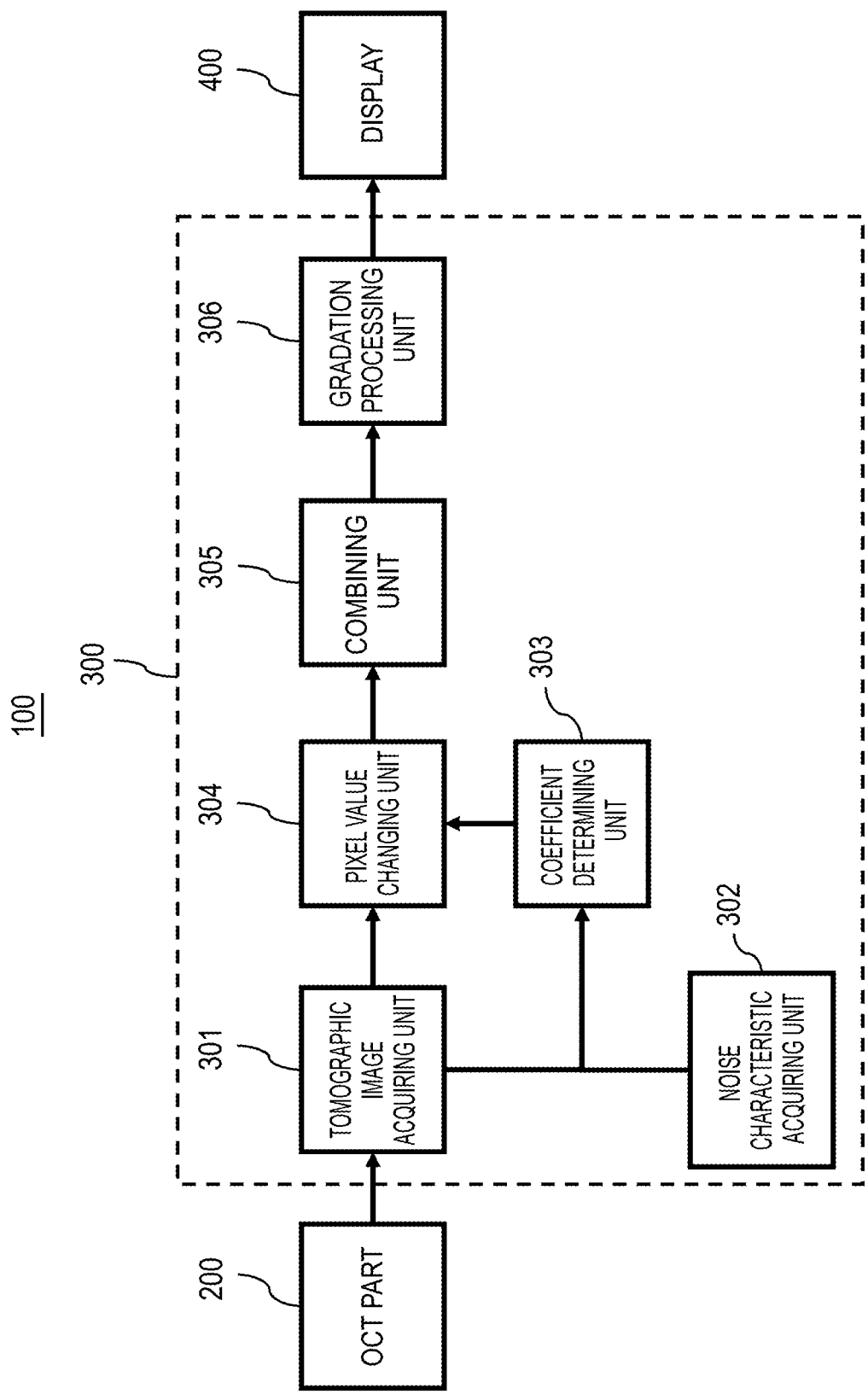
FIG. 1 is a diagram for schematically illustrating a configuration of an OCT apparatus in a first embodiment of this disclosure.

Preferred embodiments of the present invention will now be described in detail in accordance with the accompanying drawings.

Matters to be described in the following embodiments, which include dimensions, materials, shapes, and relative positions of components, can be freely set, and can be changed depending on various conditions or configurations of apparatus to which this disclosure is applied. In the drawings, the same reference symbols are used among the drawings to denote components that are the same as one another or functionally similar to one another.

First Embodiment

Now, with reference to FIG. 1 to FIG. 9B, an OCT apparatus including an image processing apparatus according to a first embodiment of this disclosure is described. FIG. 1 is a diagram for schematically illustrating the configuration of the OCT apparatus in the first embodiment. In the following description, a human eye (eye to be inspected) is taken as an object to be inspected.

An OCT apparatus 100 includes an OCT part 200, an image processing apparatus 300, and a display 400. The OCT part 200 splits light from a light source (not shown) into measuring light and reference light, scans the measuring light over the eye to be inspected, and outputs an interference signal of light from the eye to be inspected and the reference light to the image processing apparatus 300. As types of OCT, there are, for example, a spectral-domain OCT (SD-OCT) for spectrally dispersing the interference light to obtain a tomographic signal and a wavelength swept-source OCT (SS-OCT) for sweeping a wavelength of the light source. It is possible to employ the OCT part 200 that uses any one of the above-mentioned types of OCT. The configuration and function of the OCT part 200 using any one of those types of OCT are known, and hence descriptions thereof are omitted.

The image processing apparatus 300 generates a tomographic image based on the interference signal input from the OCT part 200, applies different kinds of processing described later to the tomographic image to achieve high image quality, and then outputs the tomographic image to the display 400. The image processing apparatus 300 includes a tomographic image acquiring unit 301 (data acquiring unit), a noise characteristic acquiring unit 302 (noise acquiring unit), a coefficient determining unit 303, a pixel value changing unit 304 (changing unit), a combining unit 305, and a gradation processing unit 306 (image generating unit). Those components are described later in detail.

In the first embodiment, the image processing apparatus 300 is formed of a computer connected to the OCT part 200. In addition, the respective components of the image processing apparatus 300 are formed of software modules that operate on the computer. However, the configuration of the image processing apparatus 300 is not limited to the above-mentioned configuration. All or a part of the functions of the image processing apparatus 300 may be formed of an ASIC or other such hardware having specific functions, or a graphics processing unit (GPU) may be used to speed up a part of the processing. Further, the image processing apparatus 300 may be formed of a general-purpose computer, or may be formed of a computer dedicated to the OCT apparatus 100.

The display 400 displays the tomographic image output from the image processing apparatus 300. The display 400 is formed of a liquid crystal monitor or other such display device connected to the image processing apparatus 300 and a controller (not shown) configured to drive and control the display device. In the first embodiment, the OCT part 200, the image processing apparatus 300, and the display 400 are formed separately, but a part or all of the OCT part 200, the image processing apparatus 300, and the display 400 may be integrally formed.

Figure 2:
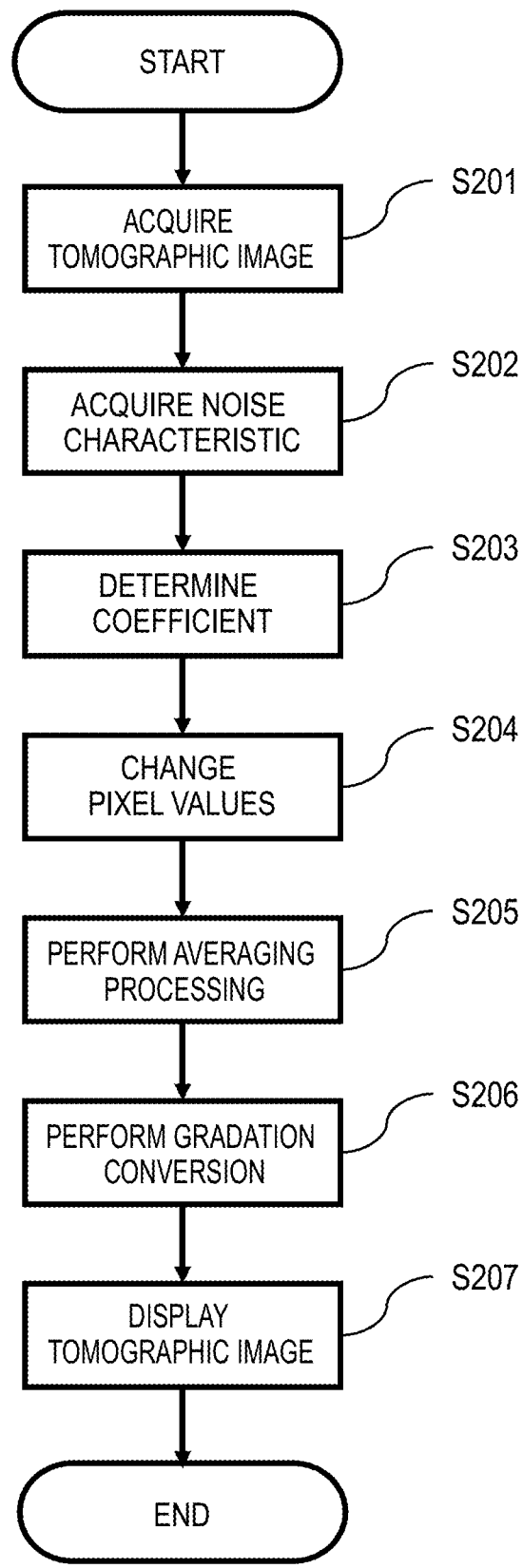
FIG. 2 is a flow chart for illustrating an operation of an image processing apparatus according to the first embodiment.

Next, with reference to FIG. 2, functional operations of the respective components of the OCT apparatus 100 are described. FIG. 2 is a flow chart for illustrating an operation of the image processing apparatus 300. In the first embodiment, it is assumed that, in the respective processing steps described below, a central processing unit (CPU) of the image processing apparatus 300 operates in accordance with a program stored in a storage apparatus (not shown) of the image processing apparatus 300 and controls the respective components, to thereby achieve the functions.

<Step S201>

First, when the image processing apparatus 300 starts the operation, in Step S201, the tomographic image acquiring unit 301 of the image processing apparatus 300 controls the OCT part 200 to acquire a tomographic image. In Step S201, the OCT part 200 irradiates the eye to be inspected with measuring light, detects interference light of return light from a fundus and reference light, and outputs the interference light as a digital interference signal.

Figure 3A:
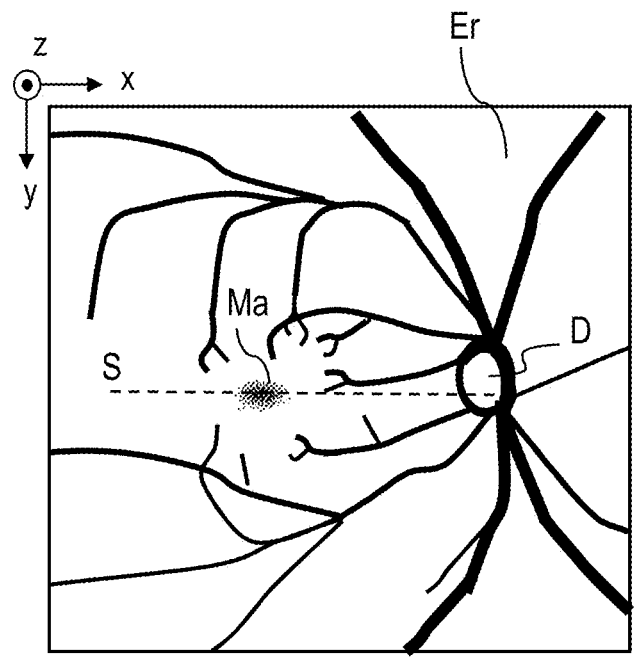
FIG. 3A and FIG. 3B are explanatory diagrams for illustrating the acquisition of a tomographic image.

In FIG. 3A, a scanning position S of the measuring light used by the OCT part 200 is indicated by the broken line in a front image of a fundus Er. As illustrated in FIG. 3A, the scanning position S is set so as to cross an optic papilla D and a macula Ma. The scanning position S is set by an inspector operating the OCT apparatus 100 based on the fundus image and the like obtained from the OCT part 200 or other image pickup apparatus. In this case, the front image of the fundus Er illustrated in FIG. 3A may be generated by integrating the interference signals acquired by the OCT part 200 in the z direction indicated in FIG. 3B, or may be generated by a fundus image pickup apparatus (not shown) provided separately from the OCT part 200. The front image of the fundus Er may also be generated based on output from an optical system for fundus image pickup, which is provided to the OCT part 200.

An operation for setting the scanning position S may also be performed by causing, for example, the image processing apparatus 300 to function as an image acquisition control apparatus. In this case, the inspector can set the scanning position S through use of a user interface displayed on the display 400. On the user interface for setting the scanning position S, as illustrated in FIG. 3A, the scanning position S is superimposed on the image of the fundus Er to be displayed, and the inspector uses a keyboard (not shown) and a mouse (not shown), which are connected to the image processing apparatus 300, to set the scanning position S at a desired position on the fundus Er. The scanning position S may be automatically set by the image processing apparatus 300 or another image acquisition control apparatus based on, for example, the fundus image and a part to be measured of the eye to be inspected.

Figure 3B:
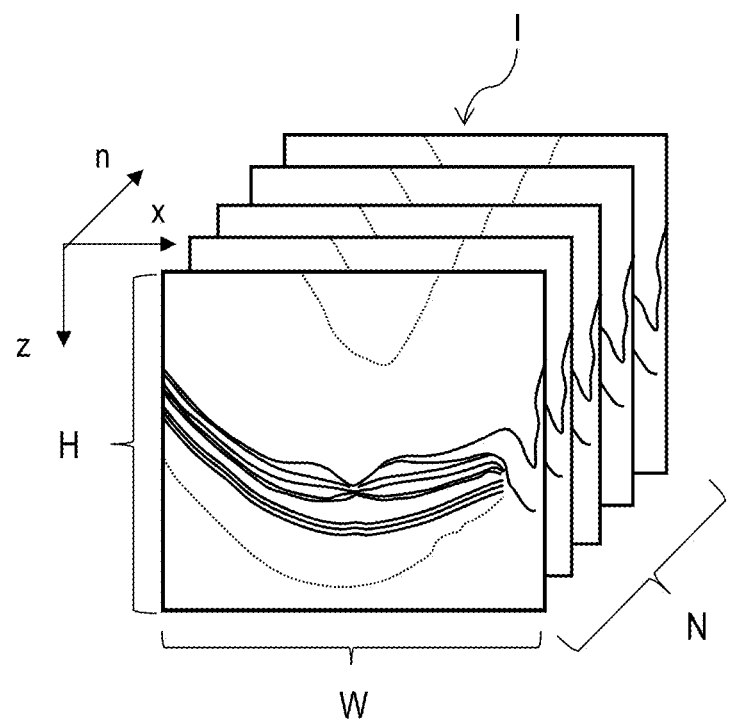

In the first embodiment, the OCT part 200 performs scanning N times at the scanning position S on the fundus Er, and outputs the detected interference signals to the tomographic image acquiring unit 301. The tomographic image acquiring unit 301 processes the input interference signals to generate a plurality of tomographic images I representing the tomographic section of the eye to be inspected as illustrated in FIG. 3B. In the first embodiment, the number of pixels of one tomographic image in the x direction (scanning direction) is set as W, and the number of pixels of one tomographic image in the z direction (depth direction) is set as H.

The value of the number N of times of scanning may be appropriately set by the inspector through the above-mentioned user interface, or may be stored in advance in the image processing apparatus 300 as a parameter specific to an imaging apparatus. For example, 100 is selected as the value of the number N of times of scanning, but this disclosure is not limited thereto, and the value can be freely set. However, statistical properties of the measurement data are used in processing described later, and hence the value of N can be set to at least about 10. In the following description, one tomographic image included in the plurality of tomographic images I is referred to as "B-scan image", and the plurality of tomographic images I are simply referred to as "tomographic image I". In this case, the term "B-scan" refers to an operation of scanning the measurement light in a predetermined transverse direction of the fundus.

The generation of a tomographic image based on an interference signal is performed by, for example, the elimination of background data, wavelength wavenumber conversion required in the case of SD-OCT, and Fourier transform. As a method of generating the tomographic image, a known method can be freely used, and hence a detailed description thereof is omitted.

While the scanning is thus performed at the same position a plurality of times, the eye to be inspected moves due to, for example, involuntary eye movement during fixation, which causes a misalignment between the B-scan images in the tomographic image I. Therefore, the tomographic image acquiring unit 301 corrects the misalignment based on the pixel values of the respective B-scan images. For example, the tomographic image acquiring unit 301 sets a region of interest in each of the B-scan images, and matches the regions of interest with each other, to thereby be able to detect the misalignment. For the detection of the misalignment and the correction of the position, known technologies can be freely used, and hence detailed descriptions thereof are omitted. The following description presupposes that respective pixels that form a B-scan image have been subjected to the correction of a spatial misalignment with respect to a different B-scan image, and that the respective B-scan images correspond to the same position of an object. The tomographic image acquiring unit 301 outputs the generated tomographic image I that has been subjected to the correction of the position to the coefficient determining unit 303 and the pixel value changing unit 304.

<Step S202>

In Step S202, the noise characteristic acquiring unit 302 acquires a characteristic of noise included in the OCT part 200 from a noise image $I_e$ generated by the tomographic image acquiring unit 301 based on an interference signal acquired by the OCT part 200 under the absence of return light from the object. The noise image $I_e$ (noise data) can be obtained as a tomographic image generated through image acquisition by blocking the measuring light to an eye to be inspected or without placing the object prior to the image acquisition of the eye to be inspected. It is not required to acquire the noise image $I_e$ each time the image of an eye to be inspected is acquired. Therefore, for example, the noise image $I_e$ may be acquired in advance at the time of the adjustment of the OCT part 200, and the noise image $I_e$ or a noise characteristic based on the noise image $I_e$, which is described later, may be stored in a hard disk drive or other such storage apparatus of the image processing apparatus 300.

Figure 4A:
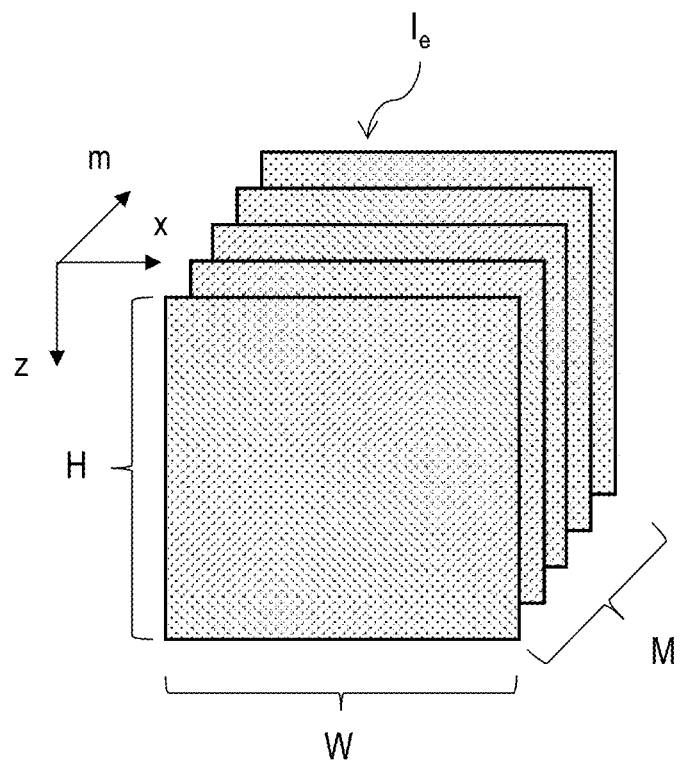
FIG. 4A and FIG. 4B are an explanatory diagram and an explanatory graph, respectively, for illustrating and showing the acquisition of a noise characteristic.

FIG. 4A is an explanatory diagram for schematically illustrating the noise image $I_e$. The noise image $I_e$ is formed of a plurality of B-scan images generated based on interference signals obtained by scanning the measuring light M times in the same manner as in the case of the tomographic image I illustrated in FIG. 3B. However, the noise image $I_e$, which has been acquired under the absence of the return light from the object, includes only noise components that occur in the course of the detection of an OCT signal performed by the OCT part 200. The number M of times of scanning may be the same as or different from the number N of times of scanning performed when the image of the eye to be inspected is acquired. However, in order to more accurately calculate the characteristic of the noise, the number M of times of scanning may be larger than the number N of times of scanning, and can be set to, for example, a value of at least 100. In the first embodiment, the number of pixels of one noise image in the x direction (scanning direction) is set to have the same value as the number W of pixels of the tomographic image in the x direction. However, the number of pixels of the noise image in the x direction is not necessarily the same as the number of pixels of the tomographic image in the x direction, and may be set to a different number.

Next, the noise characteristic acquiring unit 302 calculates a noise characteristic NF(z) corresponding to an average noise level along the z-axis from the noise image $I_e$. Specifically, the noise characteristic acquiring unit 302 uses Expression 1 to average the pixel values of each B-scan image in the noise image $I_e$ at each pixel position by the number of times of scanning, and obtains data e(z) by averaging the averaged pixel values of the B-scan image in the horizontal direction (scanning direction). After that, the noise characteristic acquiring unit 302 performs secondary polynomial fitting or other fitting processing on the data e(z) to calculate the noise characteristic NF(z).

$$e(z) = \frac{1}{w}\Sigma_x \left( \frac{1}{M}\Sigma_m I_e(x, z, m) \right) \quad \text{Expression 1}$$

Figure 4B:
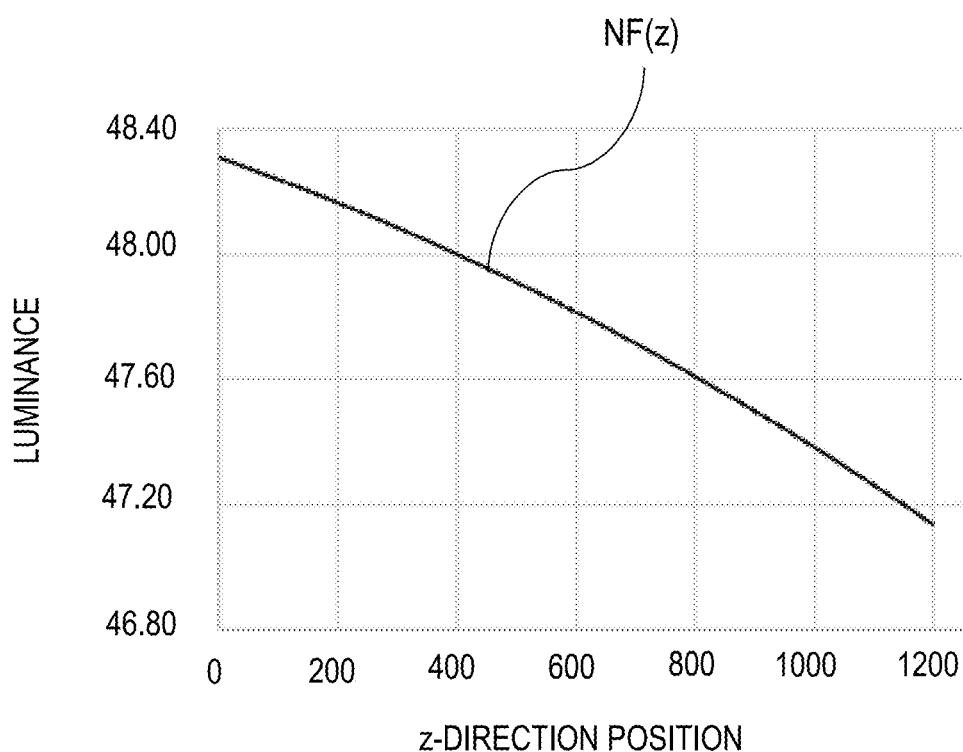

In FIG. 4B, the noise characteristic NF(z) is exemplified, and an average level of the noise along the z direction is shown. It is not required to calculate the noise characteristic NF(z) each time the image of an eye to be inspected is acquired as well, and the noise characteristic NF(z) may be calculated when the noise image $I_e$ is acquired, and stored in the hard disk drive or other such storage apparatus of the image processing apparatus 300. In this case, it is not required to store the noise image $I_e$. The noise characteristic acquiring unit 302 outputs the calculated noise characteristic NF(z) to the coefficient determining unit 303.

<Step S203>

In Step S203, the coefficient determining unit 303 calculates a weighting coefficient "w" based on the tomographic image I including a signal from the eye to be inspected input from the tomographic image acquiring unit 301 and the noise characteristic NF(z) output from the noise characteristic acquiring unit 302. More specifically, the coefficient determining unit 303 uses Expression 2 to calculate a weighting coefficient w(x,z) at each pixel position (x,z) in the tomographic image based on the tomographic image I and the noise characteristic NF(z).

$$w(x, z) = \frac{|A|}{N} \text{ where} \quad \text{Expression 2}$$
$$A = \{I(x, z, n) \mid I(x, z, n) > NF(z), 0 \leq n < N\}$$

Figure 5A:
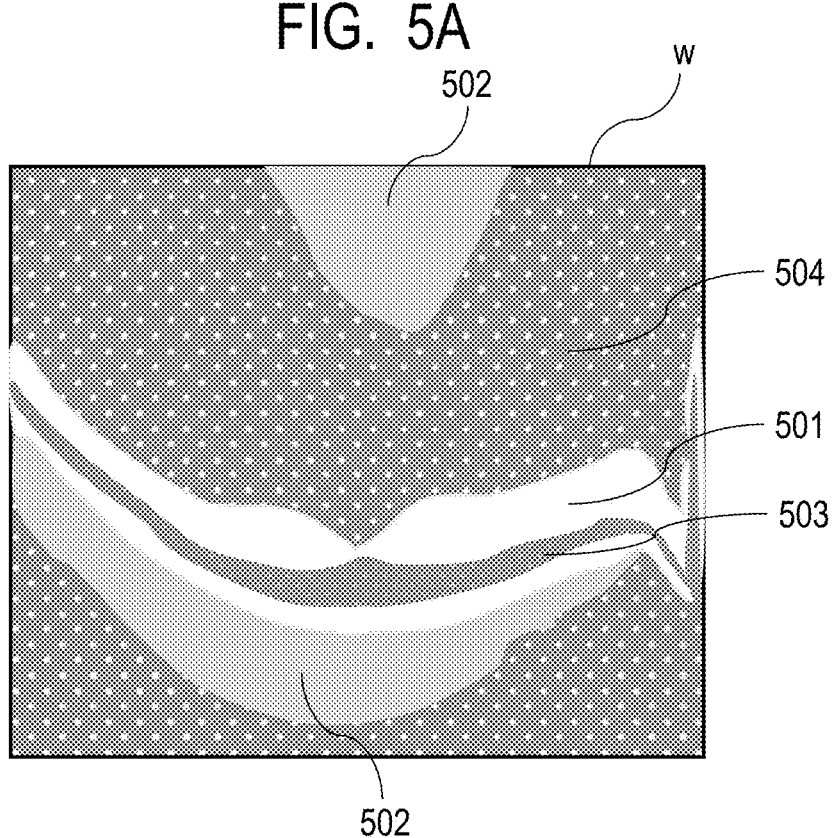
FIG. 5A is an explanatory diagram for illustrating the distribution of a weighting coefficient.

In this case, the weighting coefficient w(x,z) in the first embodiment is calculated as a ratio of the number of pixel values larger than the noise characteristics NF(z) at the same pixel position in the pixel positions that are exhibited by the pixels of the respective B-scan images in the tomographic image I. In FIG. 5A, the weighting coefficient w(x,z) is exemplified in the form of an image, and a larger value of the weighting coefficient w(x,z) is expressed as a whiter region.

Figure 5B:
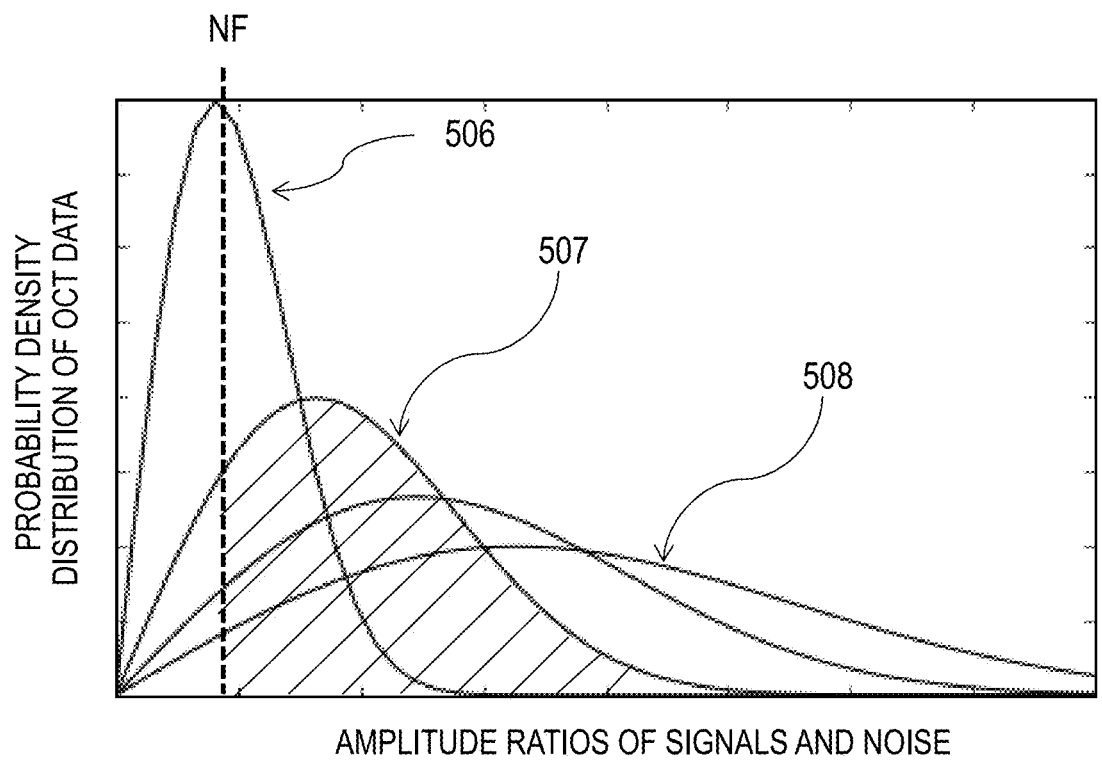
FIG. 5B is an explanatory graph for showing a probability density distribution of OCT data.

In FIG. 5A, a region 501 corresponds to an optic nerve fiber layer or other such layer exhibiting a high signal intensity within a retina, a region 502 corresponds to the structure of the vitreous body or a sclera, a region 503 corresponds to an outer granular layer being a layer within the retina, and a region 504 corresponds to a region exhibiting no signal from the object. Such a correspondence relationship between the value of the weighting coefficient "w" and the region of the tomographic section is qualitatively described with reference to FIG. 5B. FIG. 5B is a graph for showing a probability density distribution of OCT data. In FIG. 5B, a distribution 506 represents a distribution exhibited when there is no signal from the object, a distribution 507 represents a distribution exhibited when the amplitude of the signal from the object is a1, and a distribution 508 represents a distribution exhibited when the amplitude of the signal from the object is a2, which is higher than a1.

It is known that an OCT signal amplitude exhibits a Rice distribution, and the distribution changes depending on a ratio between the amplitude of a steady-state signal (signal from the object) and the amplitude of noise. As shown in FIG. 5B, a ratio at which a pixel value at a given position in the tomographic image is larger than a noise level NF calculated when there is no signal from the object is expressed as a ratio of the hatched part to the entire distribution when the signal from the object the amplitude is, for example, a1. The ratio becomes higher as the amplitude of the signal from the object becomes higher, and is considered to correspond to the signal intensity of the signal from the object included in the interference signal detected by the OCT part 200.

That is, the value of the weighting coefficient "w", which is the ratio of the number of pixel values larger than the noise characteristic NF(z) at the same pixel position in the pixel positions that are exhibited by the respective pixels, correlates to the level of the amplitude of the signal from the fundus of the eye to be inspected. Therefore, the weighting coefficient "w" is distributed in the vicinity of about 1.0 when a reflectance with respect to the measuring light is high, as in the case of an optic nerve fiber layer, and reflected light therefrom rarely falls below the noise level NF, while the weighting coefficient "w" is distributed around about 0.5 when there is no signal from the object. Meanwhile, the weighting coefficient "w" is distributed to values of from about 0.5 to about 0.8 in the case of a structure exhibiting a weak signal amplitude, for example, the structure of the vitreous body.

Figure 6:
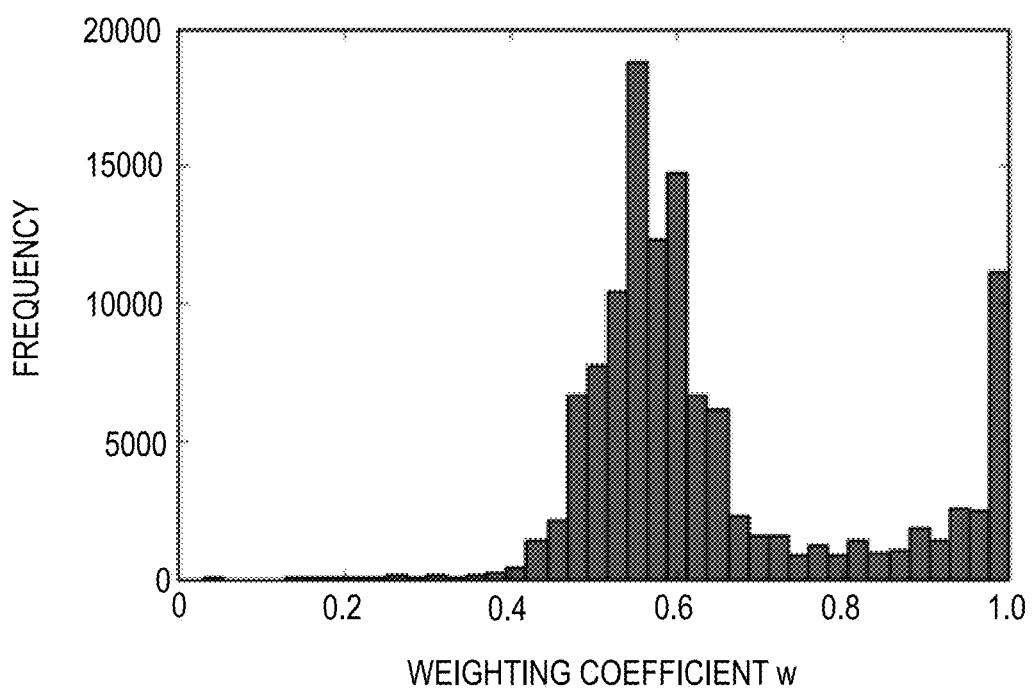
FIG. 6 is a histogram for showing the weighting coefficient.

In FIG. 6, an example of a histogram of the weighting coefficient "w" is shown. In the histogram shown in FIG. 6, the weighting coefficient "w" has a peak in the vicinity of 0.5, which corresponds to mainly a mixture of a noise component and a weak signal from the vitreous body or the like, and has a peak of in the vicinity of 1.0, which corresponds to a strong signal from the optic nerve fiber layer or the like.

The coefficient determining unit 303 may perform non-linear conversion processing on the weighting coefficient "w" to expand the distribution of the weighting coefficient "w". For example, it is possible to bring the signal amplitude corresponding to the noise component close to zero by subjecting the weighting coefficient "w" to γ-conversion with a parameter of at least 1.0. The value of γ can be determined in advance by a subjective evaluation based on the generated tomographic image or the like, and can be set to, for example, about 2.0.

The coefficient determining unit 303 outputs the weighting coefficient "w" calculated in the above-mentioned manner to the pixel value changing unit 304.

<Step S204>

In Step S204, the pixel value changing unit 304 uses Expression 3 to change the pixel values of the tomographic image I input from the tomographic image acquiring unit 301 based on the weighting coefficient "w" input from the coefficient determining unit 303.

$$I_w(x,z,n) = I(x,z,n)w(x,z) \quad \text{Expression 3}$$

The pixel value changing unit 304 may further add an offset term, which is an emphasis parameter for emphasizing a weak signal, to the value of a pixel exhibiting a weak signal, or multiply the value of the pixel by the offset term, based on the distribution of the weighting coefficient "w" as described below.

Figure 7A:
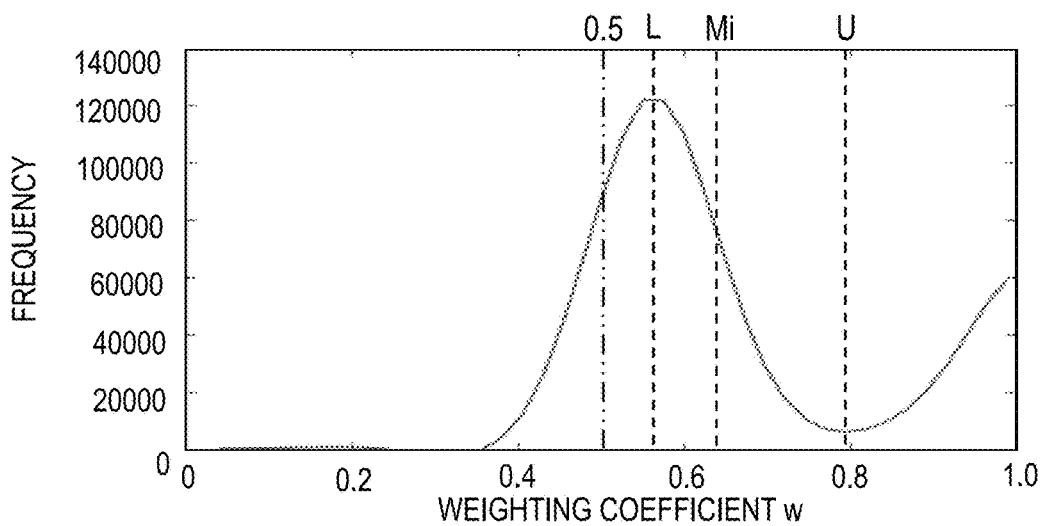
FIG. 7A, FIG. 7B, and FIG. 7C are explanatory graphs for showing an operation of a pixel value changing unit.

The pixel value changing unit 304 calculates the histogram of the weighting coefficient "w" shown in FIG. 6, and obtains two boundaries L and U shown in FIG. 7A for the range of the value of the weighting coefficient "w" based on a frequency of the histogram. In this case, FIG. 7A is a graph for showing a mathematical function into which the histogram of the weighting coefficient "w" is fitted. First, the pixel value changing unit 304 fits the frequency of the histogram of the weighting coefficient "w" by, for example, polynomial interpolation or smoothing spline, then analyzes the fitted frequency, and detects a peak in the vicinity of w=0.5 and a valley in the vicinity of w=0.7 to 0.8. The pixel value changing unit 304 obtains the peak in the vicinity of w=0.5 as the boundary L, and obtains the valley in the vicinity of w=0.7 to 0.8 as the boundary U. In this case, the peak in the vicinity of w=0.5, which is the boundary L, corresponds to an extreme value corresponding to a noise component.

Figure 7B:
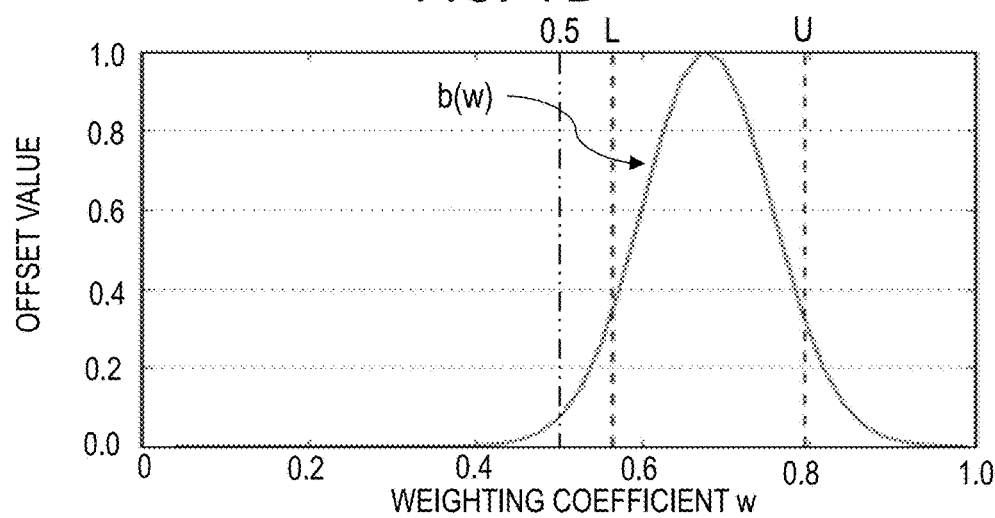

Next, as shown in FIG. 7B, the pixel value changing unit 304 calculates a distribution b(w) of the offset value as a Gaussian distribution exhibiting an average of (L+U)/2 and a standard deviation σ of ±Rσ with respect to the range of from U to L. FIG. 7B is a graph for showing the distribution b(w) of the offset value, which is calculated as the Gaussian distribution. After calculating the distribution b(w) of the offset value, the pixel value changing unit 304 uses Expression 4 to change each pixel value of the tomographic image I.

$$I_w(x,z,n)=I(x,z,n)w(x,z)+gb(w(x,z))$$ Expression 4

Expression 4 is effective in that the first term on the right-hand side relatively attenuates the noise component by the above-mentioned weighting coefficient "w", and that the second term (offset term) amplifies the weak signal amplitude of, for example, the vitreous body so as to become close to the signal level of a retinal layer. In this case, "g" is a parameter for adjusting the degree of amplification, and may be determined in advance. In the first embodiment, "g" can be set to from about 0.5 to about 2.0. In addition, the value of R may be determined in advance based on, for example, a subjective evaluation of the image obtained as a result. For example, the value of R can be set to about 1.5, and the degree of change in pixel value becomes smaller as the value becomes smaller, while the contrast is lowered when the value becomes too large.

The distribution b(w) is not limited to the above-mentioned Gaussian distribution, and any distribution that has a unimodal shape within the range of from L to U may be used as the distribution b(w). This is because noise components exhibiting amplitudes distributed around about the weighting coefficient "w" of 0.5 and pixels corresponding to a retinal region, which originally exhibit as high signal intensities as amplitudes of the weighting coefficient "w" of at least 0.8, are inhibited from being emphasized.

Figure 7C:
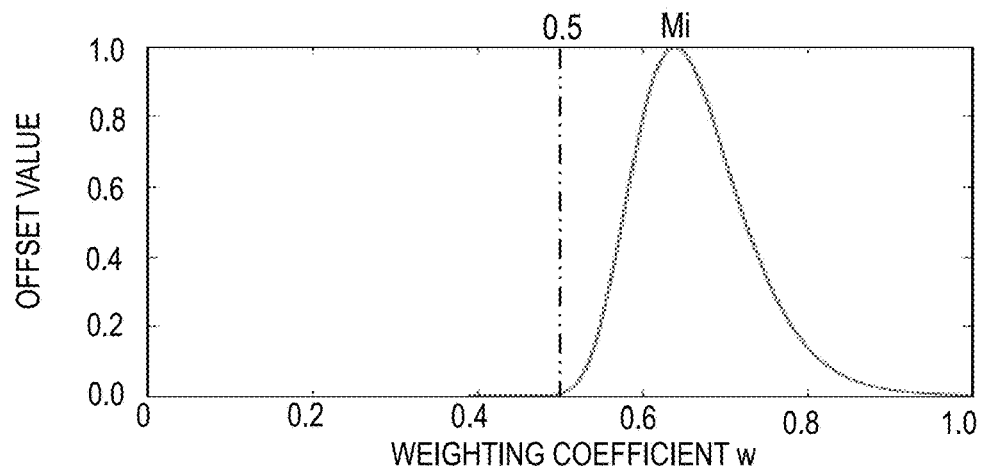

The distribution b(w) is not necessarily a symmetrical distribution, and an asymmetrical distribution distorted toward zero can be used as well. As such a distribution, for example, a logarithmic normal distribution or a Rayleigh distribution can be used. In that case, a parameter may be set so that an average of the distribution b(w) falls between L and U, for example, becomes Mi shown in FIG. 7A (for example, Mi corresponding to a weight at which the distribution exhibits the steepest gradient). FIG. 7C is a graph for showing distribution b(w) calculated as the logarithmic normal distribution. In the shown distribution b(w), the offset value steeply attenuates toward the negative direction of the weighting coefficient "w" with respect to Mi, while the offset value gradually attenuates toward the positive direction. Through use of a distribution having such a shape, the offset value is steeply attenuated for the noise components, while emphasis can be placed over a wider range for the signal from the object. The distribution b(w) may be generated by combining a plurality of distributions, which allows an offset amount to be set more flexibly.

The pixel value changing unit 304 outputs the tomographic image $I_w$, which is obtained by changing each pixel value of the tomographic image I based on Expression 3 or Expression 4, to the combining unit 305.

<Step S205>

In Step S205, the combining unit 305 averages the input tomographic image $I_w$ having the changed pixel values based on Expression 5 to generate an average tomographic image $I_{av}$. The combining unit 305 outputs the generated average tomographic image $I_{av}$ to the gradation processing unit 306.

$$I_{av}(x, z) = \frac{1}{N}\Sigma_n I_w(x, z, n)$$ Expression 5

<Step S206>

Figure 8A:
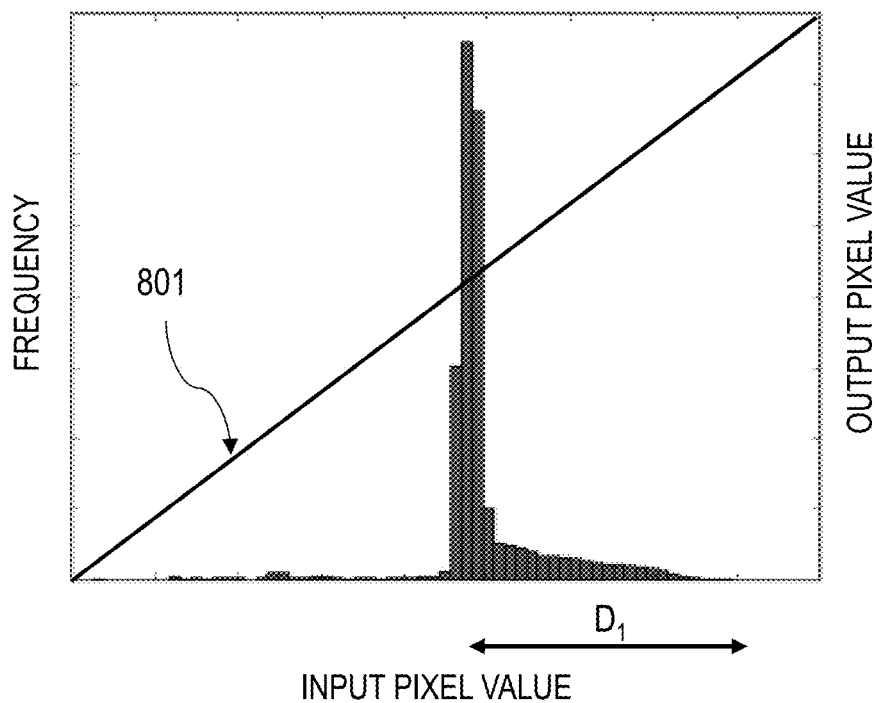
FIG. 8A and FIG. 8B are explanatory graphs for showing an operation of a gradation processing unit.
Figure 8B:
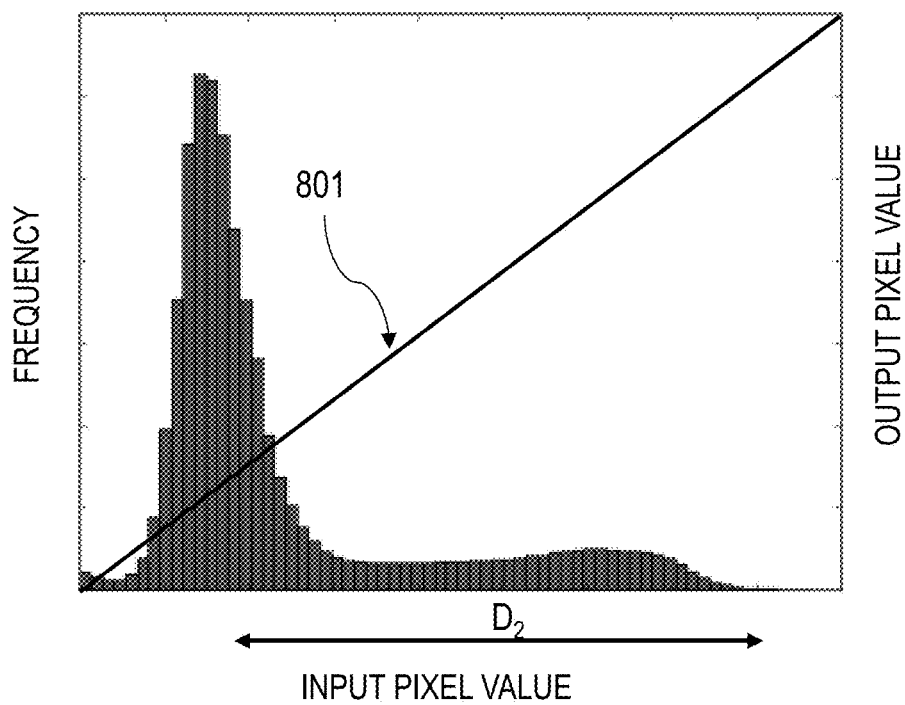

In Step S206, the gradation processing unit 306 converts a gradation of the input average tomographic image $I_{av}$ so as to fall within a range that can be displayed by the display 400. In FIG. 8A and FIG. 8B, examples of a histogram of the frequency of an average tomographic image and a gradation curve 801 are shown. In FIG. 8A, the example of the histogram of the frequency of the average tomographic image $I_{av}$ and the gradation curve 801 that are obtained when the pixel values have not been changed based on Expression 3 or Expression 4 is shown, and in FIG. 8B, the example of the histogram of the frequency of the average tomographic image $I_{av}$ and the gradation curve 801 that are obtained when the pixel values have been changed based on Expression 4 is shown. In FIG. 8A and FIG. 8B, the horizontal axis represents a pixel value relating to the histogram and an input pixel value relating to a gradation curve, and the vertical axis represents a frequency relating to the histogram and an output pixel value relating to the gradation curve.

It is understood that, as shown in FIG. 8A and FIG. 8B, a range D2 of from the noise level to the maximum luminance level in the tomographic image obtained when the pixel values have been changed is wider than a range D1 of from the noise level to the maximum luminance level in the tomographic image obtained when the pixel values have not been changed. This is because the pixel value of a pixel highly expected to exhibit noise is attenuated with respect to the distribution of data by Expression 4, which expands an entire dynamic range.

As described above, according to Expression 4, an offset is added to the pixel value of the pixel exhibiting a weak signal corresponding to a vitreous body, and hence the structure of the vitreous body is emphasized, and is visually recognized with ease. The gradation processing unit 306 generates an output tomographic image based on the gradation curve 801 shown in, for example, FIG. 8B, and outputs the output tomographic image to the display 400.

<Step S207>

Figure 9A:
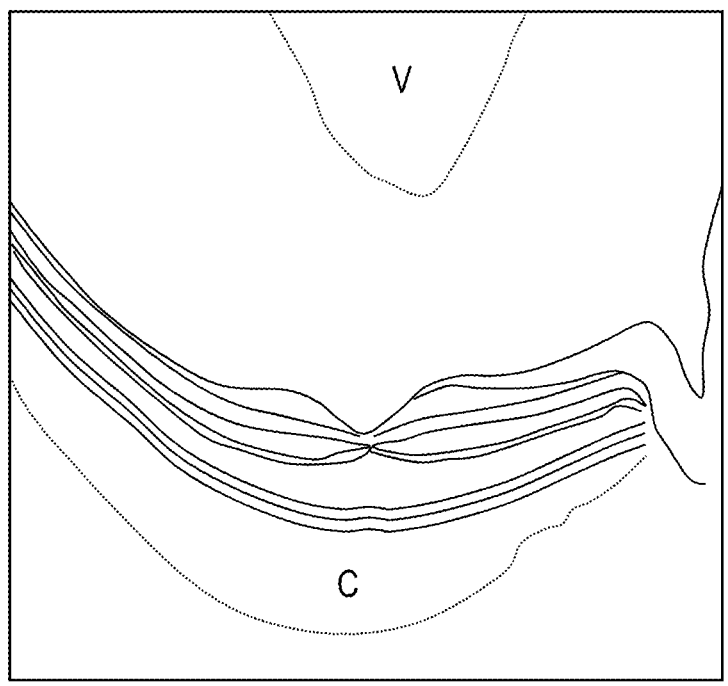
FIG. 9A is an explanatory diagram for illustrating a normally processed tomographic image.
Figure 9B:
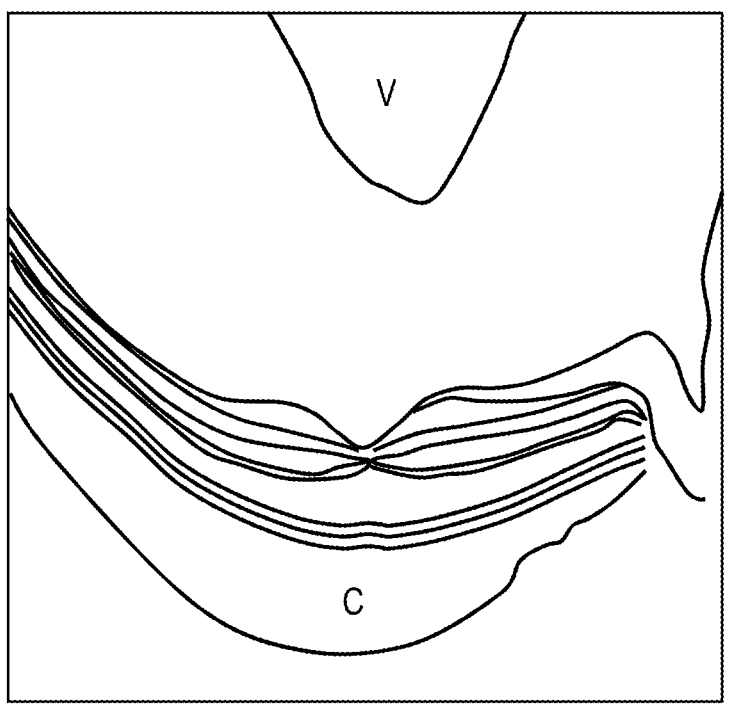
FIG. 9B is an explanatory diagram for illustrating a tomographic image subjected to image processing in the first embodiment.

In Step S207, the display 400 displays the output tomographic image input from the gradation processing unit 306 on the liquid crystal monitor or other such display device. FIG. 9A and FIG. 9B are diagrams for illustrating examples of the displayed image. FIG. 9A is a diagram for illustrating an example of the average tomographic image obtained by simply averaging tomographic images without using Expression 3 or Expression 4, and FIG. 9B is a diagram for illustrating an example of the average tomographic image to which pixel value conversion processing in the first embodiment has been applied.

As illustrated in FIG. 9B, through the application of the pixel value conversion processing in the first embodiment, weak signals relating to a vitreous body V and a choroid C can be emphasized, to thereby be able to improve the visibility of those structures. In addition, a layer boundary can be emphasized with respect to the signal from the vitreous body based on the weighting coefficient "w" without being extracted, to thereby be able to improve image quality with stability without being affected by the deformation of a retinal layer due to a disease. Even when the pixel values are changed based on Expression 3, compared to the average tomographic image obtained by simply averaging tomographic images as illustrated in FIG. 9A, it is possible to attenuate the noise components and relatively emphasize the vitreous body or other such structure, which can produce the same effects.

As described above, the image processing apparatus 300 according to the first embodiment includes the tomographic image acquiring unit 301 configured to acquire a plurality of tomographic images, which are obtained by performing optical coherence tomographic imaging of the eye to be inspected through use of the measuring light a plurality of times, and the noise characteristic acquiring unit 302 configured to acquire the noise characteristic of the tomographic image. The image processing apparatus 300 further includes the coefficient determining unit 303 configured to determine a weighting coefficient corresponding to each pixel position in the tomographic image based on the plurality of tomographic images and the noise characteristic, and the pixel value changing unit 304 configured to change pixel values of the tomographic image based on the weighting coefficient. The image processing apparatus 300 further includes the gradation processing unit 306 configured to generate an output tomographic image based on the changed pixel values. The image processing apparatus 300 further includes the combining unit 305 configured to generate an average tomographic image based on the changed pixel values, and the gradation processing unit 306 can generate the output tomographic image based on the average tomographic image.

More specifically, the noise characteristic acquiring unit 302 acquires an average noise intensity at each pixel position of the tomographic image as the noise characteristic from the noise data obtained when there is no return light of the measuring light from the eye to be inspected. After that, the coefficient determining unit 303 determines the weighting coefficient based on a ratio at which the pixel value at the same pixel position in the tomographic image exceeds the average noise intensity at the same pixel position. The pixel value changing unit 304 multiplies the pixel value of the tomographic image by the weighting coefficient, to thereby change the pixel value of the tomographic image.

Further, the pixel value changing unit 304 can also generate an emphasis parameter at each pixel position based on a distribution of the weighting coefficient to change the pixel value of the tomographic image based on the weighting coefficient and the emphasis parameter. In this case, the pixel value changing unit 304 can generate the emphasis parameter based on an extreme value in the distribution of the weighting coefficient, for example, the extreme value corresponding to a noise component. In addition, the pixel value changing unit 304 can change the pixel value of the tomographic image by multiplying the pixel value of the tomographic image by the weighting coefficient and adding the emphasis parameter to a result of the multiplication, or by multiplying the pixel value of the tomographic image by the weighting coefficient and the emphasis parameter.

According to the first embodiment, the weight is calculated for each pixel from the average level of noise (noise characteristic) and the distribution of the measurement data obtained through the image acquisition, and the pixel value based on the measurement data is multiplied by the weight, to thereby be able to attenuate the noise and relatively emphasize the weak signal from, for example, a vitreous body. The attenuated noise also enables an improvement in contrast between a signal having a high intensity, which corresponds to a retina or other such structure, and a noise region. Therefore, it is possible to simultaneously improve the contrasts of structures having a large difference in signal intensity level, for example, a vitreous body and a retina. This can efficiently optimize the contrast of an image as a whole, and can facilitate the simultaneous observation and diagnosis of the structures having a large difference in intensity level of the tomographic signal.

Further, the emphasis parameter is applied when the pixel value is changed, to thereby be able to selectively emphasize a weak signal while suppressing noise. Therefore, it is possible to selectively emphasize a vitreous body or other such structure exhibiting a signal having a signal level that greatly differs from another structure of a retina, and to simultaneously improve the contrasts of the structures having a large difference in signal intensity level.

In the above-mentioned MAP estimation, the weak signal is estimated by setting the center of the distribution as a signal amplitude. In contrast, according to the first embodiment, the noise level NF is calculated in advance, and the ratio of pixels having pixel values exceeding the noise level NF at each position in the tomographic image may be calculated as the weighting coefficient. Therefore, the processing in the first embodiment involves a calculation load that is far lighter than in the MAP estimation processing, and produces substantially the same effects in the visualization of the weak signal.

In the first embodiment, when the boundaries L and U of the frequency of the weighting coefficient "w" are obtained, the peak in the vicinity of w=0.5 and the valley in the vicinity of w=0.7 to 0.8 are obtained, but the values of "w" are merely examples. It suffices that the boundaries L and U are obtained based on the shape of the distribution of the weighting coefficient "w".

For example, the pixel value changing unit 304 detects a peak corresponding to a noise component and a peak corresponding to a signal from a retina based on the shape of the histogram of the frequency of the weighting coefficient "w", and detects a valley at which the frequency is minimum between those peaks. Then, the pixel value changing unit 304 may obtain the peak corresponding to the noise component as the boundary L, and obtain a valley between the peak corresponding to the noise component and the peak corresponding to the signal from the retina as the boundary U. A valley at which the frequency is minimum within a range in which the weighting coefficient "w" is higher than the peak corresponding to the noise component may be simply detected to be set as the boundary U.

The pixel value changing unit 304 may also obtain Mi being an average of the distribution of the offset value without obtaining the boundary U. For example, the pixel value changing unit 304 can detect the peak corresponding to the noise component and the peak corresponding to the signal from the retina, and can obtain a portion at which the gradient of the distribution b(w) is maximum between those peaks as Mi.

In addition, the pixel value changing unit 304 may detect the peak corresponding to the noise component to be set as the boundary L, and may obtain a value larger than the boundary L by a predetermined value as Mi being the average of the distribution of the offset value. The pixel value changing unit 304 may also obtain the boundary U being the valley between the peak corresponding to the noise component and the peak corresponding to the signal from the retina, and may obtain a value smaller than the boundary U by a predetermined value as Mi. Each of the boundaries U and L is not required to strictly match the peak or the valley, and may be obtained as a value before or after the peak or the valley, which substantially corresponds to the peak or the valley.

The gradation processing is not limited to the above-mentioned method, and another method may be used to perform gradation conversion. For example, contrast limited adaptive histogram equalization (CLAHE) being histogram equalization processing to be locally performed may be used.

In the CLAHE, the histogram equalization is performed by dividing an image into a plurality of rectangular regions and imposing a limitation on the contrast so as to inhibit the noise from being amplified too much. However, in a tomographic image obtained by the OCT, the distribution of the pixel value greatly differs between the retina and another region. Therefore, when the CLAHE is used for the tomographic image obtained by the OCT, in general, the contrast obtained as a result may change depending on the structure of the eye to be inspected, which is included in the rectangular region, and a boundary between regions may be observed as an artifact from the viewpoint of the entire tomographic image.

However, according to the first embodiment, the pixel value changing unit 304 converts a weak signal to be visualized so as to have a level close to that of a signal from a retinal layer. Therefore, even when the CLAHE is applied, it is possible to prevent the boundary between regions from being recognized as an artifact.

The processing in the first embodiment can also be applied to both the tomographic image I subjected to logarithmic transform after the Fourier transform and the tomographic image I in a linear state. When the processing in the first embodiment is applied to a tomographic image before the logarithmic transform, gb(w) corresponding to the offset term of Expression 4 is desired to be used for the multiplication instead of the addition.

In addition, in the first embodiment, the gradation processing unit 306 performs the gradation processing on the average tomographic image $I_{av}$ generated by the combining unit 305. However, the gradation processing unit 306 may perform the gradation processing on one B-scan image included in the tomographic image having the changed pixel values, to thereby set a result thereof as the output tomographic image. In this case, the combining unit 305 may be omitted. In relation thereto, the gradation processing unit 306 can function as the image generating unit configured to generate the output tomographic image.

The processing in the first embodiment is not limited to the processing to be applied to the tomographic image I. The processing in the first embodiment may be applied to an interference signal acquired by the OCT part 200, a signal obtained by subjecting the interference signal to the Fourier transform, a signal obtained by subjecting the above-mentioned signal to freely-selected processing, and tomographic data including the tomographic image based on those signals. Even in those cases, the same effects as those of the above-mentioned configuration can be produced. Also in those cases, the output tomographic image may be generated from average tomographic data based on a plurality of groups of pieces of tomographic data corresponding to a plurality of tomographic images, or the output tomographic image may be generated from a set of pieces of tomographic data corresponding to one tomographic image.

Second Embodiment

In the first embodiment, the noise level NF calculated in advance is used to determine the weighting coefficient "w", while in a second embodiment of this disclosure, the weighting coefficient "w" is determined based on a comparison between distributions of data. Now, processing in the second embodiment is described with reference to FIG. 10A to FIG. 11B. An OCT apparatus in the second embodiment includes the same components as those of the OCT apparatus 100 in the first embodiment, and hence the descriptions of those components are omitted by denoting the components by the same reference symbols. The processing in the second embodiment is the same as the processing in the first embodiment except for the processing performed by the noise characteristic acquiring unit 302 and the processing performed by the coefficient determining unit 303, and hence only Step S202 and Step S203 are described while descriptions of the other steps are omitted.

<Step S202>

In Step S202 in the second embodiment, the noise characteristic acquiring unit 302 acquires the characteristic of the noise included in the OCT part 200 from the noise image $I_e$ generated under the absence of an object in the same manner as in the first embodiment. However, in the second embodiment, instead of the average amplitude level of the noise, the shape of the distribution is used as the characteristic of the noise.

Figure 10A:
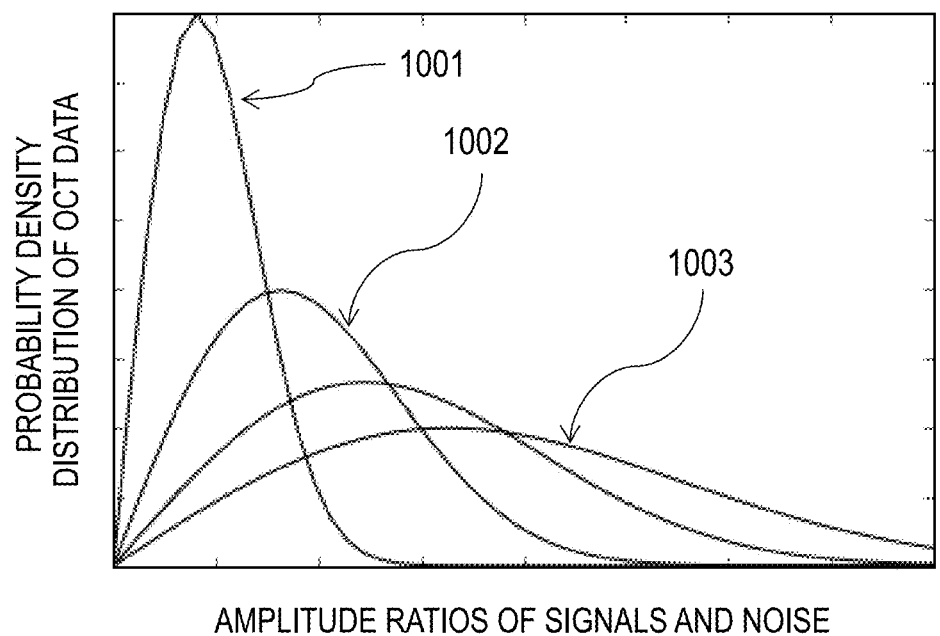
FIG. 10A and FIG. 10B are explanatory graphs for showing a method of determining a weighting coefficient in a second embodiment of this disclosure.
Figure 10B:
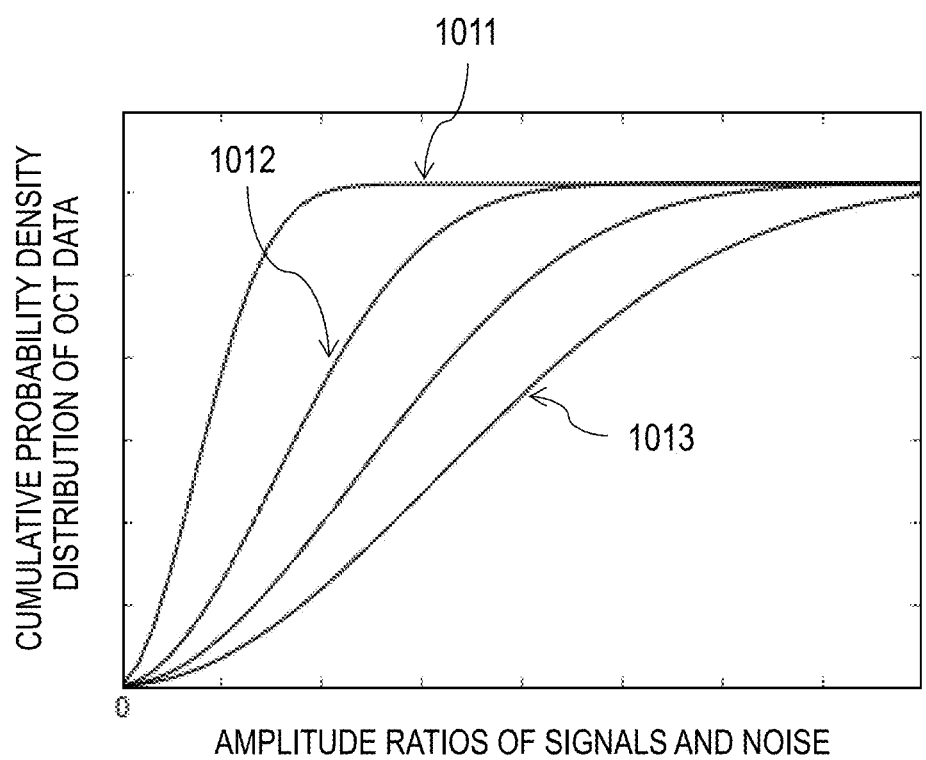

In the same manner as FIG. 5B, FIG. 10A is a graph for showing the distribution of data exhibited when OCT measurement is repeated for each of the levels of some different signal intensities. A distribution 1001 represents a distribution exhibited when there is no signal from the object, a distribution 1002 represents a distribution exhibited when the amplitude of the signal from the object is a1, and a distribution 1003 represents a distribution exhibited when the amplitude of the signal from the object is a2, which is higher than a1. FIG. 10B is a graph for showing a cumulative probability distribution of those distributions. As described in the first embodiment, the shape of the distribution of data differs depending on the difference in signal intensity, and hence the shape of the cumulative probability distribution also differs as shown in FIG. 10B. Specifically, as the signal amplitude becomes higher, the rising edge of the cumulative probability distribution becomes more gradual.

In the second embodiment, the noise characteristic acquiring unit 302 generates a reference cumulative histogram NC, which is a histogram of the cumulative probability distribution of the noise component, from the data (noise data) acquired under the absence of the object, and stores the reference cumulative histogram NC as the characteristic of the noise. In this case, the reference cumulative histogram NC corresponds to a cumulative histogram calculated from a histogram of the frequency of the noise data. The noise characteristic acquiring unit 302 may store the reference cumulative histogram NC after fitting the reference cumulative histogram NC by, for example, the polynomial interpolation or the smoothing spline.

Figure 11A:
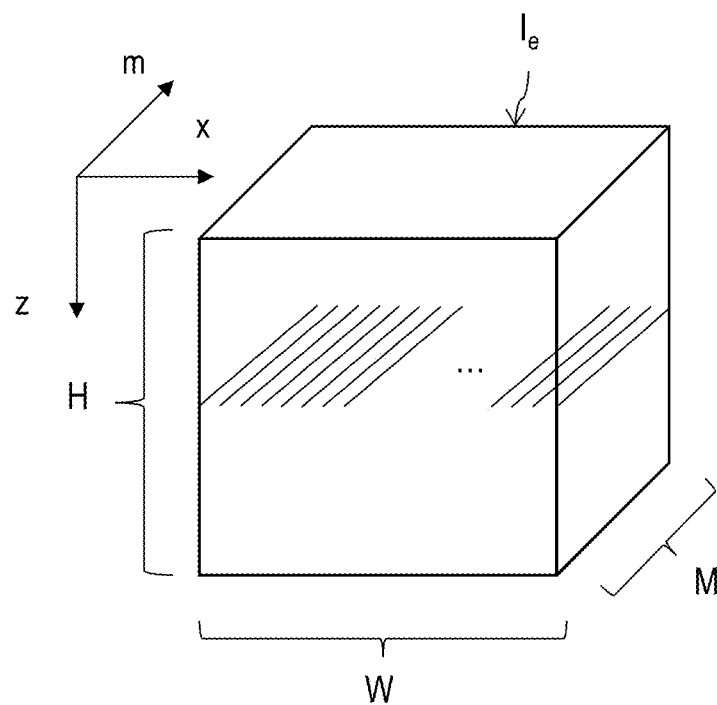
FIG. 11A and FIG. 11B are explanatory diagram for illustrating the acquisition of a noise characteristic in the second embodiment.
Figure 11B:
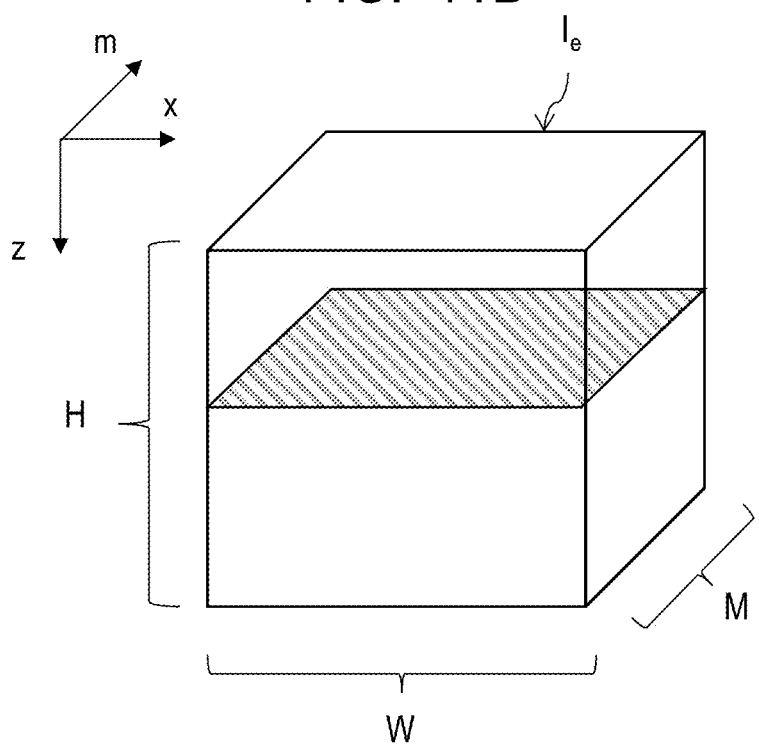

In this case, as indicated by the line segments in FIG. 11A, the noise characteristic acquiring unit 302 can calculate the cumulative histogram for each x coordinate and each z coordinate through OCT measurement repeated M times. In another case, as indicated by the hatched part in FIG. 11B, the noise characteristic acquiring unit 302 can calculate the cumulative histogram for each z coordinate with all pieces of data in the x direction being used as one set. In the second embodiment, as illustrated in FIG. 11B, the noise characteristic acquiring unit 302 calculates the cumulative histogram for each z coordinate with all pieces of data in the x direction being used as one set. In FIG. 11A and FIG. 11B, for the sake of description, "m" is illustrated as one direction axis, but as described above, "m" corresponds to the number M of times of scanning, and the measurement through the OCT is performed at the same position.

<Step S203>

In Step S203, the coefficient determining unit 303 first obtains a cumulative histogram IC(x,z), which is a histogram of the cumulative probability distribution, at each pixel position (x,z) in the tomographic image I including the signal from the eye to be inspected input from the tomographic image acquiring unit 301. In this case, the cumulative histogram IC(x,z) corresponds to the cumulative histogram calculated from the histogram of the frequency of M pieces of data corresponding to the pixel positions (x,z) of the aligned B-scan images. The cumulative histogram IC(x, z) may be obtained by the tomographic image acquiring unit 301 and output to the coefficient determining unit 303.

After that, the tomographic image acquiring unit 301 uses Expression 6 and Expression 7 to calculate the weighting coefficient w(x,z) at each pixel position in the tomographic image based on the cumulative histogram IC(x,z) at each pixel position in the tomographic image I and a reference cumulative histogram NC(z) representing the noise characteristic.

$$w'(x, z) = \max(|IC(x, z) - NC(z)|) \quad \text{Expression 6}$$

$$w(x, z) = \frac{w'(x, z)}{\max_{(x,z) \in Re} (w'(x, z))} \quad \text{Expression 7}$$

In Expression 7, Re represents the entire region of the B-scan image. When the reference cumulative histogram NC is generated and stored for each x coordinate and each z coordinate as illustrated in FIG. 11A, NC(z) of Expression 6 is NC(x,z).

The coefficient determining unit 303 outputs the calculated weighting coefficient "w" to the pixel value changing unit 304. The subsequent processing steps are the same as those of the first embodiment, and hence descriptions thereof are omitted.

The method of comparing the shapes of the distributions with each other is not limited to the method based on Expression 6. In regard to the comparison between the shapes of the distributions, any method that involves a comparison between two waveforms can be used. For example, the tomographic image acquiring unit 301 may set a correlation coefficient between two cumulative histograms as the weighting coefficient "w".

As described above, in the second embodiment, the noise characteristic acquiring unit 302 acquires the cumulative histogram of the noise at each pixel position from the noise data as the noise characteristic. After that, the coefficient determining unit 303 determines the weighting coefficient based on the cumulative histogram of the pixel values of the plurality of tomographic images and the cumulative histogram of the noise at the same pixel position.

According to the second embodiment, weighting suitable for the amplitude of the signal can be performed based on the comparison between the shapes of the distributions of OCT measurement data. Therefore, the noise component can be suppressed, and the weak signal from, for example, a vitreous body can be relatively emphasized and visualized.

The processing in the second embodiment is not limited to the processing to be applied to the tomographic image I as well, and may be applied to the above-mentioned tomographic data. Also in this case, the same effects as those of the above-mentioned configuration can be produced.

In the above-mentioned first and second embodiments, the tomographic image acquiring unit 301 acquires the interference signal acquired by the OCT part 200, and generates and acquires a tomographic image. However, the configuration of the tomographic image acquiring unit 301 as to the acquisition of the interference signal, the tomographic image, and the like is not limited thereto. For example, the tomographic image acquiring unit 301 may acquire the tomographic data including the interference signal and the tomographic image from a server or an imaging apparatus connected to the image processing apparatus 300 via, for example, a LAN, a WAN, or the Internet.

Further, the above-mentioned first and second embodiments are described by taking an eye to be inspected as an object to be inspected. However, an object to be inspected is not limited to an eye to be inspected, and may be, for example, a skin, a digestive organ, or other such organ. In this case, this disclosure can be applied not only to an ophthalmologic apparatus but also to an endoscope or other such medical equipment.

According to the first and second embodiments, it is possible to simultaneously improve the contrasts of the respective structures having a large difference in signal intensity in an OCT image of the object.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-116757, filed Jun. 14, 2017 which is hereby incorporated by reference herein in its entirety.

What is claimed is:

1. An image processing apparatus comprising:
at least one of (a) one or more processors and (b) circuitry, configured to function as a plurality of units comprising:
   (1) a data acquiring unit configured to acquire a plurality of pieces of tomographic data, which are obtained by performing optical coherence tomographic imaging of an object to be inspected through use of measuring light a plurality of times;
   (2) a noise acquiring unit configured to acquire a noise characteristic of the tomographic data;
   (3) a coefficient determining unit configured to determine a weighting coefficient at each pixel position in a tomographic image generated from the tomographic data using information regarding a number of pixels having pixel values larger than the noise characteristic, out of pixels corresponding to each other in a plurality of tomographic images generated from the plurality of pieces of tomographic data;
   (4) a changing unit configured to change a value of the tomographic data at a pixel position in accordance with the weighting coefficient; and
   (5) an image generating unit configured to generate the tomographic image based on the tomographic data that has the value changed.

2. An image processing apparatus according to claim 1, wherein the noise acquiring unit is configured to acquire the noise characteristic based on noise data obtained under absence of return light of the measuring light from the object to be inspected.

3. An image processing apparatus according to claim 2, wherein the noise acquiring unit is configured to acquire from the noise data, as the noise characteristic, an average noise intensity at each pixel position along at least one direction, and wherein the coefficient determining unit is configured to determine the weighting coefficient based on a ratio at which a pixel value of each of the pixels corresponding to each other in the plurality of tomographic images exceeds the average noise intensity at the same pixel position.

4. An image processing apparatus according to claim 1, wherein the coefficient determining unit is configured to determine the weighting coefficient based on information regarding a ratio of pixels having pixel values larger than the noise characteristic, out of the pixels corresponding to each other in the plurality of tomographic images.

5. An image processing apparatus according to claim 2, wherein the noise acquiring unit is configured to acquire from the noise data, as the noise characteristic, a cumulative histogram of noise at each pixel position along at least one direction.

6. An image processing apparatus according to claim 5, wherein the coefficient determining unit is configured to determine the weighting coefficient based on (a) a cumulative histogram of the plurality of pieces of tomographic data and (b) the cumulative histogram of the noise at the same pixel position.

7. An image processing apparatus according to claim 1, wherein the changing unit is configured to change the value of the tomographic data by multiplying the value of the tomographic data by the weighting coefficient.

8. An image processing apparatus according to claim 1, wherein the changing unit is configured to generate an emphasis parameter at the each pixel position based on a distribution of the weighting coefficient to change the value of the tomographic data based on the weighting coefficient and the emphasis parameter.

9. An image processing apparatus according to claim 8, wherein the changing unit is configured to generate the emphasis parameter based on an extreme value in the distribution of the weighting coefficient.

10. An image processing apparatus according to claim 9, wherein the changing unit is configured to generate the emphasis parameter based on the extreme value corresponding to a noise component in the distribution of the weighting coefficient.

11. An image processing apparatus according to claim 8, wherein the changing unit is configured to change the value of the tomographic data by (a) multiplying the value of the tomographic data by the weighting coefficient and (b) adding the emphasis parameter to a result of the multiplication.

12. An image processing apparatus according to claim 8, wherein the changing unit is configured to change the value of the tomographic data by multiplying the value of the tomographic data by the weighting coefficient and the emphasis parameter.

13. An image processing apparatus according to claim 1, wherein the plurality of units further comprises a combining unit configured to generate average tomographic data based on the plurality of pieces of tomographic data that has the value changed, and
wherein the image generating unit is configured to generate the tomographic image based on the average tomographic data.

14. An image processing method comprising:
acquiring a plurality of pieces of tomographic data, which are obtained by performing optical coherence tomographic imaging of an object to be inspected through use of measuring light a plurality of times;
acquiring a noise characteristic of the tomographic data;
determining a weighting coefficient at each pixel position in a tomographic image generated from the tomographic data using information regarding a number of pixels having pixel values larger than the noise characteristic, out of pixels corresponding to each other in a plurality of tomographic images generated from the plurality of pieces of tomographic data;
changing a value of the tomographic data at a pixel position in accordance with the weighting coefficient; and generating the tomographic image based on the tomographic data that has the value changed.

15. A non-transitory computer-readable storage medium having stored thereon a program for causing, when being executed by a processor, the processor to perform each step of the image processing method of claim 14.

16. An image processing apparatus according to claim 1, wherein the object to be inspected comprises a region of a vitreous body and a region of a retina.

17. A system comprising:
   an image processing apparatus according to claim 1; and
   an optical coherence tomography apparatus configured to perform the optical coherence tomographic imaging, the optical coherence tomography apparatus including a scanner arranged to scan a measuring light on the object to be inspected.

* * * * *